(12) United States Patent
Jiang et al.

(10) Patent No.: US 11,521,345 B2
(45) Date of Patent: Dec. 6, 2022

(54) METHOD AND SYSTEM FOR PROVIDING ROTATION PREVIEWS FOR THREE-DIMENSIONAL AND FOUR-DIMENSIONAL ULTRASOUND IMAGES

(71) Applicant: GE Precision Healthcare LLC, Wauwatosa, WI (US)

(72) Inventors: Zhiqiang Jiang, Jiangsu (CN); Jiajiu Yang, Jiangsu (CN)

(73) Assignee: GE PRECISION HEALTHCARE LLC, Wauwatosa, WI (US)

( * ) Notice: Subject to any disclaimer, the term of this patent is extended or adjusted under 35 U.S.C. 154(b) by 230 days.

(21) Appl. No.: 16/587,302

(22) Filed: Sep. 30, 2019

(65) Prior Publication Data
US 2021/0097753 A1    Apr. 1, 2021

(51) Int. Cl.
G06K 9/00 (2022.01)
G06T 15/08 (2011.01)
G06T 3/60 (2006.01)

(52) U.S. Cl.
CPC ............ G06T 15/08 (2013.01); G06T 3/60 (2013.01); *G06T 2200/04* (2013.01); *G06T 2207/10136* (2013.01); *G06T 2207/20092* (2013.01)

(58) Field of Classification Search
CPC . G06F 3/04845; G06T 19/00; G06T 2200/04; G06T 2219/2016; G06T 7/0012; G06T 15/08; G06T 2207/10136; G06T 2207/20092; G06T 3/60; G06T 17/00; G06T 2200/24; G06K 9/00315; G06K 15/002; G06V 20/64; G06V 40/67
See application file for complete search history.

(56) References Cited

U.S. PATENT DOCUMENTS

| | | | |
|---|---|---|---|
| 7,894,663 B2 | 2/2011 | Berg et al. | |
| 9,196,092 B2 | 11/2015 | McDermott et al. | |
| 2007/0154075 A1* | 7/2007 | Matsumoto | A61B 6/463 382/128 |
| 2009/0003665 A1* | 1/2009 | Berg | G06T 19/00 382/128 |
| 2010/0077358 A1* | 3/2010 | Sugaya | G06T 7/0012 715/838 |
| 2011/0022988 A1* | 1/2011 | Lee | H04N 21/4312 715/848 |

(Continued)

*Primary Examiner* — Guillermo M Rivera-Martinez
(74) *Attorney, Agent, or Firm* — McAndrews, Held & Malloy, Ltd.; Jacob Groethe; David Bates

(57) ABSTRACT

A system and method for presenting rotation previews of an object depicted in a volume rendering of 3D and/or 4D image data is provided. The method includes presenting a volume rendering of an object having an initial view at a display system. The method includes presenting volume rendering previews at the display system. Each of the volume rendering previews provides a different rotational view of the object and is located on the display system in relation to the volume rendering at a position associated with a directional directive of a user input device. The method includes receiving a directional directive from the user input device. The method includes presenting an updated volume rendering of the object at the display system. The updated volume rendering includes an updated view of the object rotated from the initial view based on the directional directive from the user input device.

20 Claims, 6 Drawing Sheets

(56) References Cited

U.S. PATENT DOCUMENTS

| | | | | |
|---|---|---|---|---|
| 2012/0123266 A1* | 5/2012 | Kim | ............... | A61B 8/5207 |
| | | | | 600/443 |
| 2012/0245465 A1* | 9/2012 | Hansegard | ............ | A61B 8/483 |
| | | | | 600/443 |
| 2013/0329978 A1* | 12/2013 | McDermott | ............ | G06T 15/08 |
| | | | | 382/131 |
| 2014/0195963 A1* | 7/2014 | Cheung | ............... | G06F 30/00 |
| | | | | 715/838 |
| 2017/0148227 A1* | 5/2017 | Alsaffar | ............... | G06T 11/60 |
| 2018/0033193 A1* | 2/2018 | Goel | ............... | G06T 15/04 |
| 2018/0058843 A1* | 3/2018 | Tabuchi | ............... | G01B 21/04 |
| 2018/0315238 A1* | 11/2018 | Le Doux | ............... | G06T 19/20 |
| 2019/0156526 A1* | 5/2019 | Liu | ............... | G06T 19/20 |
| 2020/0138518 A1* | 5/2020 | Lang | ............... | A61B 90/37 |

\* cited by examiner

METHOD AND SYSTEM FOR PROVIDING ROTATION PREVIEWS FOR THREE-DIMENSIONAL AND FOUR-DIMENSIONAL ULTRASOUND IMAGES

FIELD

Certain embodiments relate to ultrasound imaging. More specifically, certain embodiments relate to a method and system for providing rotation previews of objects depicted in a volume rendering of three-dimensional (3D) and/or four-dimensional (4D) image data. The rotation previews may be displayed in relation to a current view at locations corresponding with rotation directions applied via a user input device.

BACKGROUND

Ultrasound imaging is a medical imaging technique for imaging organs and soft tissues in a human body. Ultrasound imaging uses real time, non-invasive high frequency sound waves to produce two-dimensional (2D), three-dimensional (3D), and/or four-dimensional (4D) (i.e., real-time/continuous 3D images) images.

Ultrasound imaging is a valuable, non-invasive tool for diagnosing various medical conditions. Acquired ultrasound data may be analyzed and/or processed to detect anatomical structures evaluated by a medical professional to perform the diagnosis. In cases where the ultrasound image is a volume rendering of 3D or 4D image data, a user may rotate the object depicted in the volume rendering to obtain a desired view. However, users may have difficulty associating a desired rotation of an object depicted in the volume rendering with the appropriate user input device directional input.

Further limitations and disadvantages of conventional and traditional approaches will become apparent to one of skill in the art, through comparison of such systems with some aspects of the present disclosure as set forth in the remainder of the present application with reference to the drawings.

BRIEF SUMMARY

A system and/or method is provided for presenting rotation previews of an object depicted in a volume rendering of 3D and/or 4D image data in relation to a current view of the object at locations corresponding with directional directives of a user input device, substantially as shown in and/or described in connection with at least one of the figures, as set forth more completely in the claims.

These and other advantages, aspects and novel features of the present disclosure, as well as details of an illustrated embodiment thereof, will be more fully understood from the following description and drawings.

DETAILED DESCRIPTION

Figure 1:
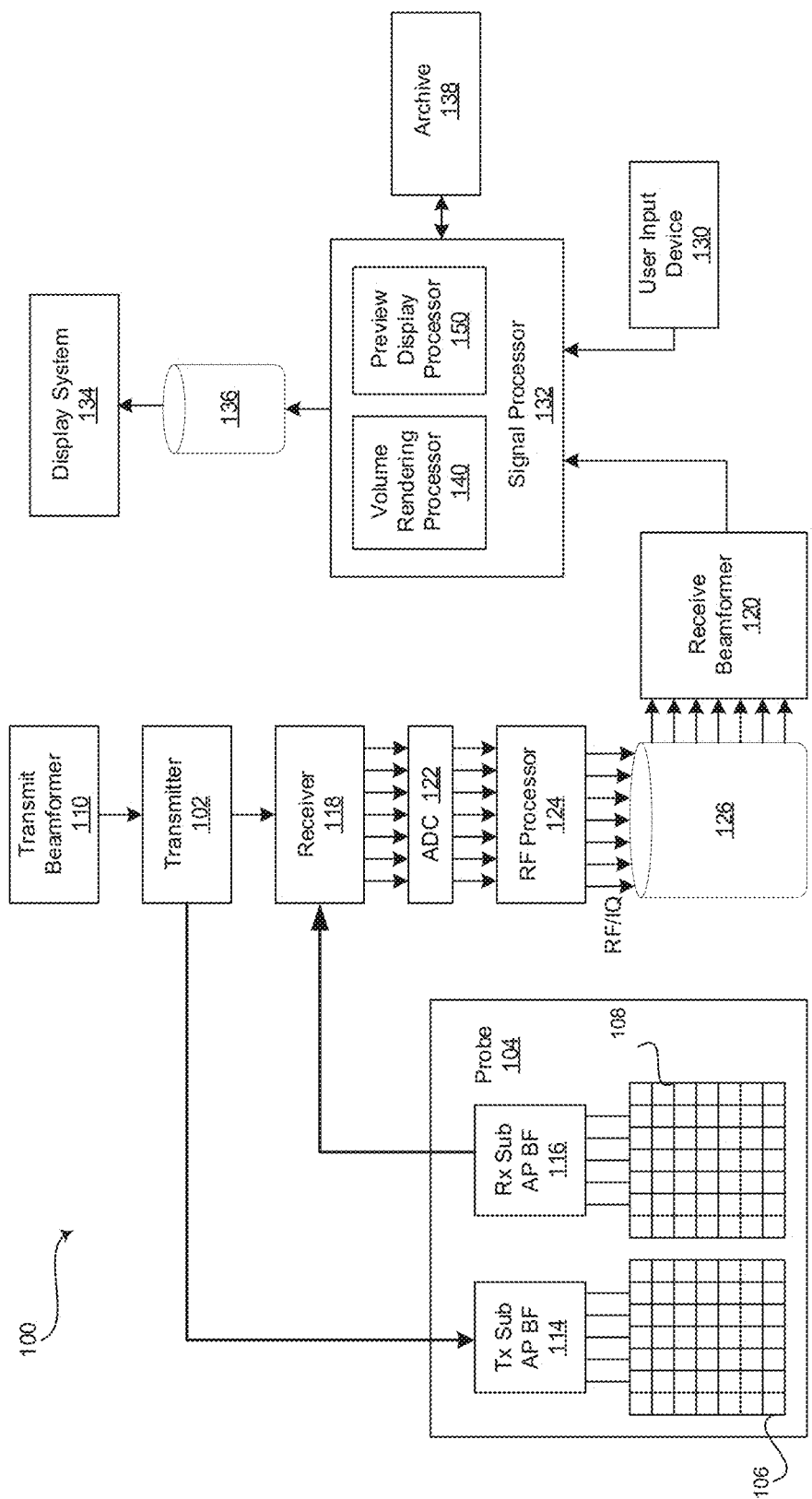
FIG. 1 is a block diagram of an exemplary ultrasound system that is operable to present rotation previews of an object depicted in a volume rendering of 3D and/or 4D image data, in accordance with various embodiments.

Certain embodiments may be found in a method and system for providing rotation previews of objects depicted in a volume rendering of three-dimensional (3D) and/or four-dimensional (4D) image data. Various embodiments have the technical effect of presenting rotation previews of the object depicted in the volume rendering of 3D and/or 4D image data in relation to a current view of the object at locations corresponding with directional directives of a user input device. Aspects of the present disclosure provide a user with an understanding of a relationship between a particular rotational direction of the object depicted in the volume rendering of the 3D and/or 4D image data and the corresponding directional directive of the user input device.

The foregoing summary, as well as the following detailed description of certain embodiments will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general-purpose signal processor or a block of random access memory, hard disk, or the like) or multiple pieces of hardware. Similarly, the programs may be stand-alone programs, may be incorporated as subroutines in an operating system, may be functions in an installed software package, and the like. It should be understood that the various embodiments are not limited to the arrangements and instrumentality shown in the drawings. It should also be understood that the embodiments may be combined, or that other embodiments may be utilized and that structural, logical and electrical changes may be made without departing from the scope of the various embodiments. The following detailed description is, therefore, not to be taken in a limiting sense, and the scope of the present disclosure is defined by the appended claims and their equivalents.

As used herein, an element or step recited in the singular and preceded with the word "a" or "an" should be understood as not excluding plural of said elements or steps, unless such exclusion is explicitly stated. Furthermore, references to "an exemplary embodiment," "various embodiments," "certain embodiments," "a representative embodiment," and the like are not intended to be interpreted as excluding the existence of additional embodiments that also incorporate the recited features. Moreover, unless explicitly stated to the contrary, embodiments "comprising," "including," or "having" an element or a plurality of elements having a particular property may include additional elements not having that property.

Also as used herein, the term "image" broadly refers to both viewable images and data representing a viewable image. However, many embodiments generate (or are configured to generate) at least one viewable image. In addition, as used herein, the phrase "image" is used to refer to an ultrasound mode such as B-mode (2D mode), M-mode, three-dimensional (3D) mode, CF-mode, PW Doppler, CW Doppler, MGD, and/or sub-modes of B-mode and/or CF such as Shear Wave Elasticity Imaging (SWEI), TVI, Angio, B-flow, BMI, BMI_Angio, and in some cases also MM, CM, TVD where the "image" and/or "plane" includes a single beam or multiple beams.

Furthermore, the term processor or processing unit, as used herein, refers to any type of processing unit that can carry out the required calculations needed for the various embodiments, such as single or multi-core: CPU, Accelerated Processing Unit (APU), Graphics Board, DSP, FPGA, ASIC or a combination thereof.

It should be noted that various embodiments described herein that generate or form images may include processing for forming images that in some embodiments includes beamforming and in other embodiments does not include beamforming. For example, an image can be formed without beamforming, such as by multiplying the matrix of demodulated data by a matrix of coefficients so that the product is the image, and wherein the process does not form any "beams". Also, forming of images may be performed using channel combinations that may originate from more than one transmit event (e.g., synthetic aperture techniques).

In various embodiments, ultrasound processing to form images is performed, for example, including ultrasound beamforming, such as receive beamforming, in software, firmware, hardware, or a combination thereof. One implementation of an ultrasound system having a software beamformer architecture formed in accordance with various embodiments is illustrated in FIG. 1.

FIG. 1 is a block diagram of an exemplary ultrasound system 100 that is operable to present rotation previews of an object depicted in a volume rendering of 3D and/or 4D image data, in accordance with various embodiments. Referring to FIG. 1, there is shown an ultrasound system 100. The ultrasound system 100 comprises a transmitter 102, an ultrasound probe 104, a transmit beamformer 110, a receiver 118, a receive beamformer 120, A/D converters 122, a RF processor 124, a RF/IQ buffer 126, a user input device 130, a signal processor 132, an image buffer 136, a display system 134, and an archive 138.

The transmitter 102 may comprise suitable logic, circuitry, interfaces and/or code that may be operable to drive an ultrasound probe 104. The ultrasound probe 104 may comprise a two dimensional (2D) array of piezoelectric elements. The ultrasound probe 104 may comprise a group of transmit transducer elements 106 and a group of receive transducer elements 108, that normally constitute the same elements. In certain embodiment, the ultrasound probe 104 may be operable to acquire ultrasound image data covering at least a substantial portion of an anatomy, such as the heart, a blood vessel, or any suitable anatomical structure.

The transmit beamformer 110 may comprise suitable logic, circuitry, interfaces and/or code that may be operable to control the transmitter 102 which, through a transmit sub-aperture beamformer 114, drives the group of transmit transducer elements 106 to emit ultrasonic transmit signals into a region of interest (e.g., human, animal, underground cavity, physical structure and the like). The transmitted ultrasonic signals may be back-scattered from structures in the object of interest, like blood cells or tissue, to produce echoes. The echoes are received by the receive transducer elements 108.

The group of receive transducer elements 108 in the ultrasound probe 104 may be operable to convert the received echoes into analog signals, undergo sub-aperture beamforming by a receive sub-aperture beamformer 116 and are then communicated to a receiver 118. The receiver 118 may comprise suitable logic, circuitry, interfaces and/or code that may be operable to receive the signals from the receive sub-aperture beamformer 116. The analog signals may be communicated to one or more of the plurality of A/D converters 122.

The plurality of A/D converters 122 may comprise suitable logic, circuitry, interfaces and/or code that may be operable to convert the analog signals from the receiver 118 to corresponding digital signals. The plurality of A/D converters 122 are disposed between the receiver 118 and the RF processor 124. Notwithstanding, the disclosure is not limited in this regard. Accordingly, in some embodiments, the plurality of A/D converters 122 may be integrated within the receiver 118.

The RF processor 124 may comprise suitable logic, circuitry, interfaces and/or code that may be operable to demodulate the digital signals output by the plurality of A/D converters 122. In accordance with an embodiment, the RF processor 124 may comprise a complex demodulator (not shown) that is operable to demodulate the digital signals to form I/Q data pairs that are representative of the corresponding echo signals. The RF or I/Q signal data may then be communicated to an RF/IQ buffer 126. The RF/IQ buffer 126 may comprise suitable logic, circuitry, interfaces and/or code that may be operable to provide temporary storage of the RF or I/Q signal data, which is generated by the RF processor 124.

The receive beamformer 120 may comprise suitable logic, circuitry, interfaces and/or code that may be operable to perform digital beamforming processing to, for example, sum the delayed channel signals received from RF processor 124 via the RF/IQ buffer 126 and output a beam summed signal. The resulting processed information may be the beam summed signal that is output from the receive beamformer 120 and communicated to the signal processor 132. In accordance with some embodiments, the receiver 118, the plurality of A/D converters 122, the RF processor 124, and the beamformer 120 may be integrated into a single beamformer, which may be digital. In various embodiments, the ultrasound system 100 comprises a plurality of receive beamformers 120.

The user input device 130 may be utilized to input patient data, scan parameters, settings, select protocols and/or templates, initiate a rotation preview display, rotate image views of depicted objects, and the like. In an exemplary embodiment, the user input device 130 may be operable to configure, manage and/or control operation of one or more components and/or modules in the ultrasound system 100. In this regard, the user input device 130 may be operable to configure, manage and/or control operation of the transmitter 102, the ultrasound probe 104, the transmit beamformer 110, the receiver 118, the receive beamformer 120, the RF processor 124, the RF/IQ buffer 126, the user input device 130, the signal processor 132, the image buffer 136, the display system 134, and/or the archive 138. The user input device 130 may include button(s), rotary encoder(s), a touchscreen, a touch pad, a trackball, motion tracking, voice recognition, a mousing device, keyboard, camera and/or any other device capable of receiving a user directive. In certain embodiments, one or more of the user input devices 130 may be integrated into other components, such as the display system 134, for example. As an example, user input device 130 may include a touchscreen display.

In various embodiments, rotation previews of objects depicted in a volume rendering of 3D or 4D image data may be displayed in response to a directive received via the user input device 130. In certain embodiments, objects captured in 3D or 4D image data may be rotated to provide a different view in response to a directive received via the user input device 130. For example, the user input device 130 may be manipulated to rotate the viewing angle of an object left, right, up, down, and/or diagonally.

The signal processor 132 may comprise suitable logic, circuitry, interfaces and/or code that may be operable to process ultrasound scan data (i.e., summed IQ signal) for generating ultrasound images for presentation on a display system 134. The signal processor 132 is operable to perform one or more processing operations according to a plurality of selectable ultrasound modalities on the acquired ultrasound scan data. In an exemplary embodiment, the signal processor 132 may be operable to perform display processing and/or control processing, among other things. Acquired ultrasound scan data may be processed in real-time during a scanning session as the echo signals are received. Additionally or alternatively, the ultrasound scan data may be stored temporarily in the RF/IQ buffer 126 during a scanning session and processed in less than real-time in a live or off-line operation. In various embodiments, the processed image data can be presented at the display system 134 and/or may be stored at the archive 138. The archive 138 may be a local archive, a Picture Archiving and Communication System (PACS), or any suitable device for storing images and related information.

The signal processor 132 may be one or more central processing units, microprocessors, microcontrollers, and/or the like. The signal processor 132 may be an integrated component, or may be distributed across various locations, for example. In an exemplary embodiment, the signal processor 132 may comprise a volume rendering processor 140 and a preview display processor 150. The signal processor 132 may be capable of receiving input information from a user input device 130 and/or archive 138, generating an output displayable by a display system 134, and manipulating the output in response to input information from a user input device 130, among other things. The signal processor 132, including the volume rendering processor 140 and the preview display processor 150, may be capable of executing any of the method(s) and/or set(s) of instructions discussed herein in accordance with the various embodiments, for example.

The ultrasound system 100 may be operable to continuously acquire ultrasound scan data at a frame rate that is suitable for the imaging situation in question. Typical frame rates range from 20-120 but may be lower or higher. The acquired ultrasound scan data may be displayed on the display system 134 at a display-rate that can be the same as the frame rate, or slower or faster. An image buffer 136 is included for storing processed frames of acquired ultrasound scan data that are not scheduled to be displayed immediately. Preferably, the image buffer 136 is of sufficient capacity to store at least several minutes' worth of frames of ultrasound scan data. The frames of ultrasound scan data are stored in a manner to facilitate retrieval thereof according to its order or time of acquisition. The image buffer 136 may be embodied as any known data storage medium.

The signal processor 132 may include a volume rendering processor 140 that comprises suitable logic, circuitry, interfaces and/or code that may be operable to perform volume rendering on 3D and/or 4D volumes. The volume rendering processor 140 may be used to generate and present volume renderings (e.g., 2D projections) of the volumetric (e.g., 3D and/or 4D) datasets. In this regard, rendering a 2D projection of a 3D and/or 4D dataset may comprise setting or defining a perception angle in space relative to the object being displayed, and then defining or computing necessary information (e.g., opacity and color) for every voxel in the dataset. This may be done, for example, using suitable transfer functions for defining RGBA (red, green, blue, and alpha) value for every voxel. The resulting volume rendering may include a depth map correlating a depth value to each pixel in the 2D projection.

In various embodiments, the volume rendering processor 140 may be configured to render 3D and/or 4D volumes into multiple viewing angles. For example, the volume rendering processor 140 may generate a first volume rendering at a current or initial viewing direction and may generate additional volume renderings (also referred to as volume rendering previews) at viewing angles offset from the initial viewing direction. The viewing angle offset may be, for example, 10 to 60 degrees or any suitable viewing angle offset that conveys to a user a rotational direction of the object depicted in the volume renderings. The number of additional volume renderings may be two (2), four (4), eight (8), or any suitable number of volume rendering previews associated with rotation directions that correspond to directional directives of a user input device 130. As an example, in addition to the first volume rendering at the initial viewing direction, the volume rendering processor 140 may be configured to generate an additional volume rendering rotated to the left, an additional volume rendering rotated to the right, an additional volume rendering rotated up, an additional volume rendering rotated down, and/or additional volume renderings rotated in diagonal directions. In certain embodiments, the number and/or orientations of the viewing angles may be pre-defined. In an exemplary embodiment, the volume rendering processor 140 may be configured to present the first volume rendering at the initial viewing direction at the display system 134 and/or may store the first volume rendering at archive 138 and/or any suitable storage medium. The additional volume renderings previewing the rotational directions of the object may be provided to the preview display processor 150 for presentation at the display system 134 as described below. Additionally and/or alternatively, the additional volume renderings may be stored at archive 138 and/or at any suitable storage medium.

In a representative embodiment, the volume rendering processor 140 may be configured to generate additional sets of volume renderings. For example, the volume rendering processor 140 may generate an updated or current volume rendering at an updated viewing angle in response to a user directive provided by the user input device 130 to, for example, rotate the viewing angle of an object left, right, up, down, and/or diagonally. In various embodiments, the volume rendering processor 140 may be configured to generate, store, and/or smoothly display updated volume renderings of the object as the viewing angle is rotated via the user input device 130. The volume rendering processor 140 may be configured to generate additional volume rendering previews at viewing angles offset from the updated viewing direction. The additional volume rendering previews may be provided to the preview display processor 150 and/or stored at a storage medium, such as archive 138.

The signal processor 132 may include a preview display processor 150 that comprises suitable logic, circuitry, interfaces and/or code that may be operable to present volume renderings previewing the rotation of an object in relation to a current volume rendering view of the object. The volume rendering previews may be presented by the preview display processor 150 at locations on the display system 134 corresponding with directional directives of the user input device 130. The volume rendering previews may provide a user with an understanding of a relationship between a particular rotational direction of the object depicted in the volume rendering and the corresponding directional directive of the user input device 130. The preview display processor 150 may receive the volume renderings previewing the object rotated at viewing angles offset from the current viewing direction from the volume rendering processor 140.

The preview display processor 150 may be configured to present each additional volume rendering preview at a location on the display system 134 in relation to the current volume rendering that corresponds to the directional directive of the user input device 130. For example, the preview display processor 150 may receive a volume rendering previewing a rotation of the viewing angle of an object to the left and a manipulation of the user input device 130 to the left may achieve a rotation in the direction of the volume rendering preview. Accordingly, the preview display processor 150 may present the volume rendering to the left of the current volume rendering on the display system 134 so that a user understands that the user input device 130 is manipulated to the left to achieve the desired rotational direction. As another example, the preview display processor 150 may receive a volume rendering previewing an upward rotation of the viewing angle of an object and a manipulation of the user input device 130 in an upward direction may achieve a rotation in the direction of the volume rendering preview. Accordingly, the preview display processor 150 may present the volume rendering above the current volume rendering on the display system 134 so that a user understands that the user input device 130 is manipulated up to achieve the desired rotational direction. The user input device 130 may be a trackball, touch pad, arrow keys on a keyboard, and/or any suitable user input device 130 capable of receiving a directional directive.

In various embodiments, the preview display processor 150 may be configured to simultaneously display each of the additional volume rendering previews at the appropriate locations on the display system 134. The preview display processor 150 may present the additional volume rendering previews automatically with the current volume rendering. Additionally and/or alternatively, the preview display processor 150 may present the additional volume rendering previews in response to a user input received from the user input device 130. For example, the user may actuate a trackball button, place a finger on a touch pad, depress a pre-determined key on a keypad, or the like, and the preview display processor 150 may present the additional volume rendering previews in response to the user input from the user input device 130. The options to automatically present the additional volume rendering previews or to present the additional volume rendering previews in response to a user directive may be a user configurable setting. In certain embodiments, the preview display processor 150 may update each of the additional volume rendering previews in lock step as the initial volume rendering is updated in response to a directional directive provided by the user input device 130 to rotate the viewing angle of the object. Alternatively, the preview display processor 150 may cease presenting the additional volume rendering previews in response to a directional directive provided by the user input device 130 to rotate the viewing angle of the object. The options to continue displaying the updated additional volume rendering previews or to cease displaying the additional volume rendering previews in response to a directional directive provided by the user input device 130 may be a user configurable setting.

The display system 134 may be any device capable of communicating visual information to a user. For example, a display system 134 may include a liquid crystal display, a light emitting diode display, and/or any suitable display or displays. The display system 134 can be operable to display information from the signal processor 132 and/or archive 138, such as medical images or any suitable information.

The archive 138 may be one or more computer-readable memories integrated with the ultrasound system 100 and/or communicatively coupled (e.g., over a network) to the ultrasound system 100, such as a Picture Archiving and Communication System (PACS), a server, a hard disk, floppy disk, CD, CD-ROM, DVD, compact storage, flash memory, random access memory, read-only memory, electrically erasable and programmable read-only memory and/or any suitable memory. The archive 138 may include databases, libraries, sets of information, or other storage accessed by and/or incorporated with the signal processor 132, for example. The archive 138 may be able to store data temporarily or permanently, for example. The archive 138 may be capable of storing medical image data, data generated by the signal processor 132, and/or instructions readable by the signal processor 132, among other things. In various embodiments, the archive 138 stores 3D and/or 4D volumes, volume renderings generated by the volume rendering processor 140, preview display parameters and settings, instructions for performing volume rendering, and/or instructions for presenting additional volume rendering previews at appropriate locations on a display system 134, among other things.

Figure 2:
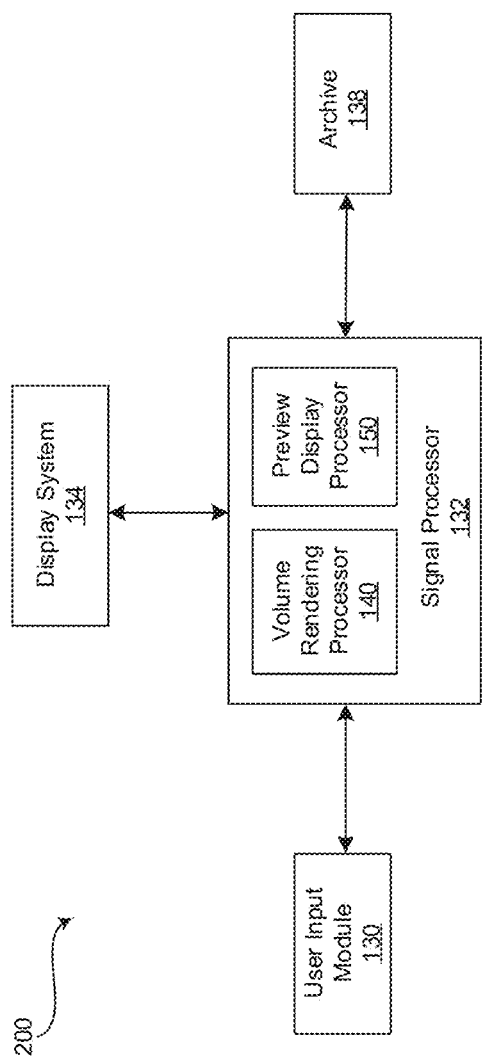
FIG. 2 is a block diagram of an exemplary medical workstation that is operable to present rotation previews of an object depicted in a volume rendering of 3D and/or 4D image data, in accordance with various embodiments.

FIG. 2 is a block diagram of an exemplary medical workstation 200 that is operable to present rotation previews of an object depicted in a volume rendering of 3D and/or 4D image data, in accordance with various embodiments. In various embodiments, components of the medical workstation 200 may share various characteristics with components of the ultrasound system 100, as illustrated in FIG. 1 and described above. Referring to FIG. 2, the medical workstation 200 comprises a display system 134, a signal processor 132, an archive 138, and a user input device 130, among other things. Components of the medical workstation 200 may be implemented in software, hardware, firmware, and/or the like. The various components of the medical workstation 200 may be communicatively linked. Components of the medical workstation 200 may be implemented separately and/or integrated in various forms. For example, the display system 134 and the user input device 130 may be integrated as a touchscreen display.

The display system 134 may be any device capable of communicating visual information to a user. For example, a display system 134 may include a liquid crystal display, a light emitting diode display, and/or any suitable display or displays. The display system 134 can be operable to display information from the signal processor 132 and/or archive 138, such as medical images or any suitable information.

The signal processor 132 may be one or more central processing units, microprocessors, microcontrollers, and/or the like. The signal processor 132 may be an integrated component, or may be distributed across various locations, for example. The signal processor 132 comprises a volume rendering processor 140 and a preview display processor 150, as described above with reference to FIG. 1, and may be capable of receiving input information from a user input device 130 and/or archive 138, generating an output displayable by a display system 134, and manipulating the output in response to input information from a user input device 130, among other things. The signal processor 132, volume rendering processor 140, and/or preview display processor 150 may be capable of executing any of the method(s) and/or set(s) of instructions discussed herein in accordance with the various embodiments, for example.

The archive 138 may be one or more computer-readable memories integrated with the medical workstation 200 and/or communicatively coupled (e.g., over a network) to the medical workstation 200, such as a Picture Archiving and Communication System (PACS), a server, a hard disk, floppy disk, CD, CD-ROM, DVD, compact storage, flash memory, random access memory, read-only memory, electrically erasable and programmable read-only memory and/or any suitable memory. The archive 138 may include databases, libraries, sets of information, or other storage accessed by and/or incorporated with the signal processor 132, for example. The archive 138 may be able to store data temporarily or permanently, for example. The archive 138 may be capable of storing medical image data, data generated by the signal processor 132, and/or instructions readable by the signal processor 132, among other things. In various embodiments, the archive 138 stores 3D and/or 4D volumes, volume renderings generated by the volume rendering processor 140, preview display parameters and settings, instructions for performing volume rendering, and/or instructions for presenting additional volume rendering previews at appropriate locations on a display system 134, among other things.

The user input device 130 may include any device(s) capable of communicating information from a user and/or at the direction of the user to the signal processor 132 of the medical workstation 200, for example. As discussed above with respect to FIG. 1, the user input device 130 may include a touch panel, button(s), a mousing device, keyboard, rotary encoder, trackball, touch pad, camera, voice recognition, and/or any other device capable of receiving a user directive.

Figure 3:
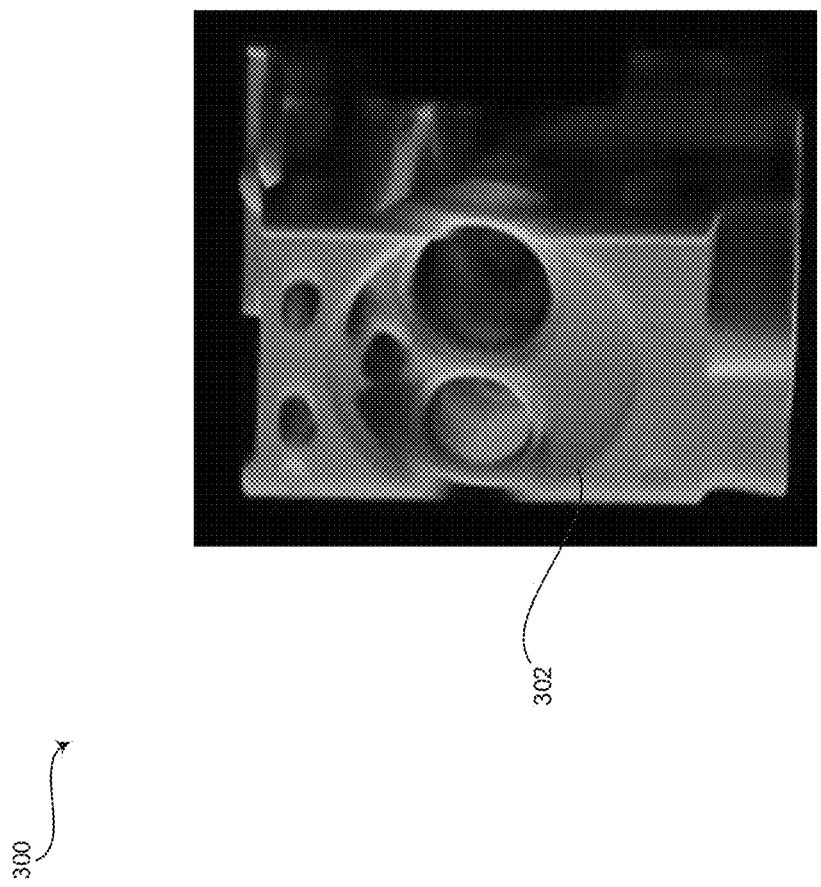
FIG. 3 is an exemplary display of an object depicted in a volume rendering of 3D and/or 4D image data, in accordance with various embodiments.

FIG. 3 is an exemplary display 300 of an object depicted in a volume rendering 302 of 3D and/or 4D image data, in accordance with various embodiments. Referring to FIG. 3, the display 300 includes a volume rendering 302 of 3D and/or 4D image data depicting an object at an initial or current viewing direction. In various embodiments, the 3D and/or 4D image data may be ultrasound image data.

Figure 4:
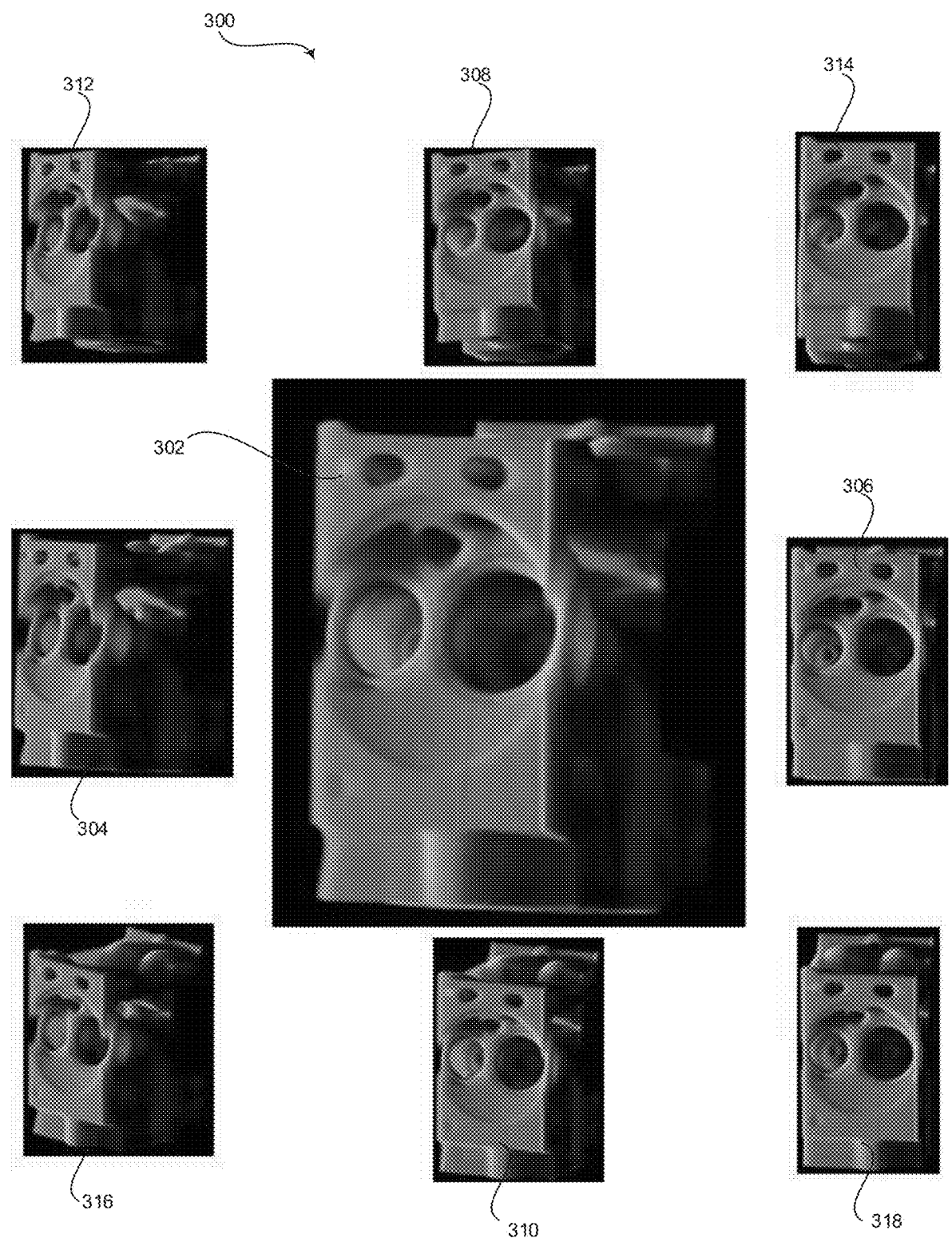
FIG. 4 is an exemplary display of rotation previews located in relation to the volume rendering of FIG. 3 at positions associated with directional directives of a user input device that provides the corresponding object rotation, in accordance with various embodiments.

FIG. 4 is an exemplary display 300 of rotation previews 304-318 located in relation to the volume rendering 302 of FIG. 3 at positions associated with directional directives of a user input device 130 that provides the corresponding object rotation, in accordance with various embodiments. Referring to FIG. 4, the display 300 includes the volume rendering 302 of FIG. 3, volume rendering previews 304-310 of the object depicted in the volume rendering 302 rotated to the left 304, right 306, up 308, and down 310, respectively, and volume rendering previews 312-318 of the object depicted in the volume rendering 302 rotated diagonally to the up and left 312, up and right 314, down and left 316, and down and right 318, respectively. Each of the volume rendering previews 304-318 are located on display 300 at a position corresponding with a directional directive of the user input device 130. For example, the object depicted in the current volume rendering 302 may update to rotate in the left direction as shown by volume rendering preview 304 when a user input device 130 provides a directional directive in a left direction. In various embodiments, the volume rendering previews 304-318 may be presented on display 300 automatically, in response to a user directive, and/or at any suitable time and/or based on any suitable trigger. In certain embodiments, the initial volume rendering 302 may update to provide an updated volume rendering depicting the rotation of the object in response to a directional directive received from the user input device 130. In an exemplary embodiment, the volume rendering previews 304-318 may update in lock step as the initial volume rendering 302 is updated. Additionally and/or alternatively, the volume rendering previews 304-318 may cease being presented once the user input device provides a directional directive for rotating the object depicted in in the initial or current volume rendering 302.

Figure 5:
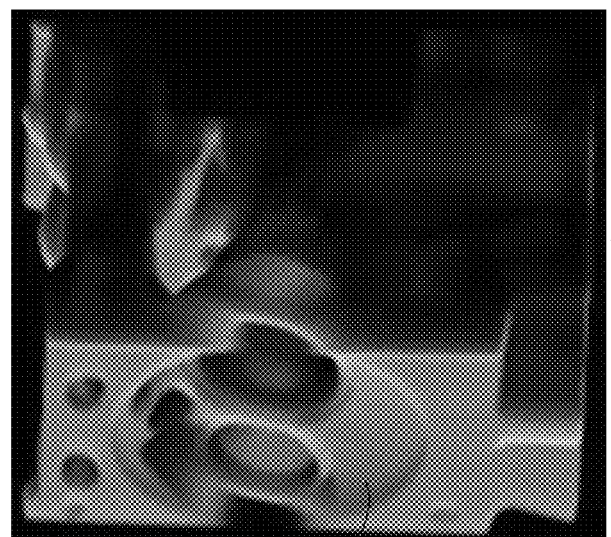
FIG. 5 is an exemplary display of the object depicted in the volume rendering of FIG. 3 after object rotation, in accordance with various embodiments.

FIG. 5 is an exemplary display 300 of the object depicted in the volume rendering 302 of FIG. 3 after object rotation, in accordance with various embodiments. Referring to FIG. 5, the display 300 includes a volume rendering 302 of 3D and/or 4D image data depicting an object at a viewing direction rotated to the left from the initial viewing direction show in FIG. 3. For example, the volume rendering 302 viewing direction is in a direction similar to the volume rendering preview 304 corresponding with rotation to the left.

Figure 6:
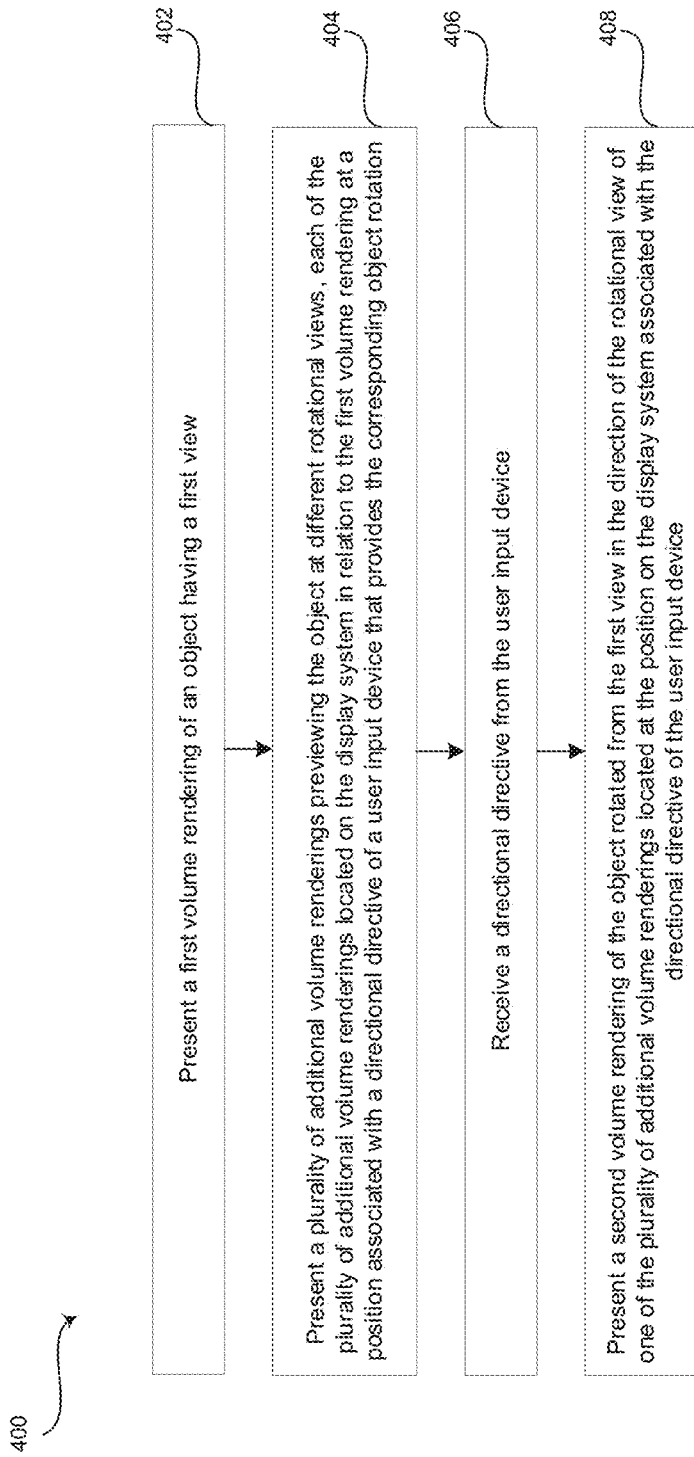
FIG. 6 is a flow chart illustrating exemplary steps that may be utilized for rotating the view of an object depicted in a volume rendering of 3D and/or 4D image data, in accordance with exemplary embodiments.

FIG. 6 is a flow chart 400 illustrating exemplary steps 402-408 that may be utilized for rotating the view of an object depicted in a volume rendering 302 of 3D and/or 4D image data, in accordance with exemplary embodiments. Referring to FIG. 4, there is shown a flow chart 400 comprising exemplary steps 402 through 408. Certain embodiments may omit one or more of the steps, and/or perform the steps in a different order than the order listed, and/or combine certain of the steps discussed below. For example, some steps may not be performed in certain embodiments. As a further example, certain steps may be performed in a different temporal order, including simultaneously, than listed below.

At step 402, a signal processor 132 of an ultrasound system 100 or medical workstation 200 may present a first volume rendering 302 of an object having a first view. For example, the ultrasound system 100 may acquire 3D and/or 4D volumes with an ultrasound probe 104. The ultrasound probe 104 may provide the acquired 3D and/or 4D volumes to the signal processor 132. A volume rendering processor 140 of the signal processor 132 may render the 3D and/or 4D volumes into the first volume rendering 302 at a current or initial viewing direction and present the volume rendering 302 at a display system 134 of the ultrasound system 100 or medical workstation 200. As another example, the signal processor 132 of the medical workstation 200 or ultrasound system 100 may retrieve 3D and/or 4D volumes from an archive 138 or any suitable data storage medium. The volume rendering processor 140 of the signal processor 132 may render the 3D and/or 4D volumes into the first volume rendering 302 at a current or initial viewing direction and present the volume rendering 302 at a display system 134 of the ultrasound system 100 or medical workstation 200.

At step 404, the signal processor 132 of the ultrasound system 100 or workstation 200 may present a plurality of additional volume renderings 304-318 previewing the object at different rotational views. Each of the additional volume renderings 304-318 may be located on the display system 134 in relation to the first volume rendering 302 at a position associated with a directional directive of a user input device 130 that provides the corresponding object rotation. For example, a preview display processor 150 of the signal processor 132 may receive volume rendering previews 304-318 from the volume rendering processor 140 and may present each of the volume rendering previews 304-318 at an appropriate location on the display system 134 corresponding to the directional directive from the user input device 130 that achieves rotation in the direction depicted in the respective volume rendering preview 304-318. The volume rendering previews 304-318 may be presented simultaneously. The volume rendering previews 304-318 may be presented in response to a user directive or automatically, for example.

At step 406, the signal processor 132 of the ultrasound system 100 or workstation 200 may receive a directional directive from the user input device 130. For example, a volume rendering processor 140 of the signal processor 132 may be configured to receive a directional directive from the user input device 130 to rotate the viewing angle of the object depicted in the volume rendering 302. As an example, a user may desire to view the object depicted in the initial volume rendering 302 rotated in a direction depicted in one of the volume rendering previews 304-318. The user may provide a directional directive at the user input device 130 corresponding with the direction of the desired volume rendering preview 304-318 from the initial volume rendering 302 on the display system 134. For example, the user may provide a directional directive to the left using the user input device 130 if the desired rotational direction of the object is depicted in the volume rendering preview 304 to the left of the initial volume rendering 302.

At step 408, the signal processor 132 of the ultrasound system 100 or workstation 200 may present a second volume rendering 302 of the object rotated from the first view in the direction of the rotational view of one of the plurality of additional volume renderings located at the position on the display system 134 associated with the directional directive of the user input device 130. For example, the volume rendering processor 140 of the signal processor 132 may generate an updated volume rendering 302 at a rotated viewing angle corresponding with the directional directive received from the user input device 130 at step 406. As an example, the volume rendering processor 140 may generate a volume rendering 302 with the viewing angle rotated to the right if the user provided a directional directive to the right at step 406. The volume rendering processor 140 may generate and display the updated volume rendering 302 at the display system 134 continuously and substantially in real-time as directional directives are received from the user input device 130. The volume rendering processor 140 may present the updated volume renderings 302 at the display system 134 as a smooth rotation of the object depicted in the volume renderings 302.

Aspects of the present disclosure provide a method 400 and system 100, 200 for presenting rotation previews 304-318 of an object depicted in a volume rendering 302 of 3D and/or 4D image data. In accordance with various embodiments, the method 400 may comprise presenting 402, by the at least one processor 132, 140, a volume rendering 302 of an object having an initial view at a display system 134. The method 400 may comprise presenting 404, by the at least one processor 132, 150, a plurality of volume rendering previews 304-318 at the display system 134. Each of the plurality of volume rendering previews 304-318 may provide a different rotational view of the object. Each of the plurality of volume rendering previews 304-318 may be located on the display system 134 in relation to the volume rendering 302 at a position associated with a directional directive of a user input device 130. The method 400 may comprise receiving 406, by the at least one processor 132, 140, 150, a directional directive from the user input device 130. The method 400 may comprise presenting 408, by the at least one processor 132, 140, an updated volume rendering 302 of the object at the display system 134. The updated volume rendering 302 may include an updated view of the object rotated from the initial view based on the directional directive from the user input device 130.

In an exemplary embodiment, the volume rendering 302 is an ultrasound image. In a representative embodiment, the method 400 may comprise rendering 402, 408, by the at least one processor 132, 140, a three-dimensional (3D) or four-dimensional (4D) volume to generate the volume rendering 302 and the updated volume rendering 302. In various embodiments, the different rotational view of the object is provided for each of the plurality of volume rendering previews 304-318 by offsetting a viewing angle from the initial view by a pre-defined amount. In certain embodiments, the plurality of volume rendering previews 304-318 is presented automatically. In an exemplary embodiment, the plurality of volume rendering previews 304-318 are presented in response to a user directive received from the user input device 130. In various embodiments, the plurality of volume rendering previews 304-318 are updated in lock step with the presentation of the updated volume rendering 302. In certain embodiments, the plurality of volume rendering previews 304-318 are removed from the display system 134 in response to the direction directive received from the user input device 130.

Various embodiments provide a system 100, 200 for presenting rotation previews 304-318 of an object depicted in a volume rendering 302 of 3D and/or 4D image data. The system 100, 200 may comprise a user input device 130, at least one processor 132, 140, 150 and a display system 134. The user input device 130 may be configured to provide a directional directive. The at least one processor 132, 140 may be configured to present a volume rendering 302 of an object having an initial view at the display system 134.

The at least one processor 132, 150 may be configured to present a plurality of volume rendering previews 304-318 at the display system 134. Each of the plurality of volume rendering previews 304-318 may provide a different rotational view of the object. Each of the plurality of volume rendering previews 304-318 may be located on the display system 134 in relation to the volume rendering 302 at a position associated with one of a plurality of directional directives of the user input device 130. The at least one processor 132, 140, 150 may be configured to receive the directional directive from the user input device 130. The at least one processor 132, 140 may be configured to present an updated volume rendering 302 of the object at the display system 134. The updated volume rendering may include an updated view of the object rotated from the initial view based on the directional directive from the user input device 130. The display system 134 may be configured to display 300 the volume rendering 302, the plurality of volume rendering previews 304-318, and the updated volume rendering 302.

In a representative embodiment, the system 100, 200 is an ultrasound system 100 or a medical workstation 200. In various embodiments, the at least one processor 132, 140, 150 is configured to provide the different rotational view of the object for each of the plurality of volume rendering previews 304-318 by offsetting a viewing angle from the initial view by a pre-defined amount. In certain embodiment, the at least one processor 132, 150 is configured to automatically present the plurality of volume rendering previews 304-318. In an exemplary embodiment, the user input device 130 may be configured to provide a user directive. The at least one processor 132, 150 may be configured to present the plurality of volume rendering previews 304-318 in response to the user directive received from the user input device 130. In a representative embodiment, the at least one processor 132, 140, 150 is configured to update the plurality of volume rendering previews 304-318 in lock step with the presentation of the updated volume rendering 302. In various embodiment, the at least one processor 132, 150 is configured to cease displaying the plurality of volume rendering previews 304-318 at the display system 134 in response to the direction directive received from the user input device 130.

Certain embodiments provide a non-transitory computer readable medium having stored thereon, a computer program having at least one code section. The at least one code section is executable by a machine for causing the machine to perform steps 400. The steps 400 may comprise presenting 402 a volume rendering 302 of an object having an initial view at a display system 134. The steps 300 may comprise presenting 404 a plurality of volume rendering previews 304-318 at the display system 134. Each of the plurality of volume rendering previews 304-318 may provide a different rotational view of the object. Each of the plurality of volume rendering previews 304-318 may be located on the display system 134 in relation to the volume rendering 302 at a position associated with a directional directive of a user input device 130. The steps 400 may comprise receiving 406 a directional directive from the user input device 130. The steps 400 may comprise presenting 408 an updated volume rendering 302 of the object at the display system 134. The updated volume rendering 302 may include an updated view of the object rotated from the initial view based on the directional directive from the user input device 130.

In various embodiments, the steps 400 may comprise offsetting 404 a viewing angle from the initial view by a pre-defined amount to provide the different rotational view of the object for each of the plurality of volume rendering previews 304-318. In certain embodiments, the plurality of volume rendering previews 304-318 are presented 300 in response to a user directive received from the user input device 130. In an exemplary embodiment, the steps 400 may comprise updating 408 the plurality of volume rendering previews 304-318 in lock step with the presentation of the updated volume rendering 302. In a representative embodiment, the steps 400 may comprise removing 408 the plurality of volume rendering previews 304-318 from the display system 134 in response to the direction directive received from the user input device 130.

As utilized herein the term "circuitry" refers to physical electronic components (i.e. hardware) and any software and/or firmware ("code") which may configure the hardware, be executed by the hardware, and or otherwise be associated with the hardware. As used herein, for example, a particular processor and memory may comprise a first "circuit" when executing a first one or more lines of code and may comprise a second "circuit" when executing a second one or more lines of code. As utilized herein, "and/or" means any one or more of the items in the list joined by "and/or". As an example, "x and/or y" means any element of the three-element set $\{(x), (y), (x, y)\}$. As another example, "x, y, and/or z" means any element of the seven-element set $\{(x), (y), (z), (x, y), (x, z), (y, z), (x, y, z)\}$. As utilized herein, the term "exemplary" means serving as a non-limiting example, instance, or illustration. As utilized herein, the terms "e.g.," and "for example" set off lists of one or more non-limiting examples, instances, or illustrations. As utilized herein, circuitry is "operable" or "configured" to perform a function whenever the circuitry comprises the necessary hardware and code (if any is necessary) to perform the function, regardless of whether performance of the function is disabled, or not enabled, by some user-configurable setting.

Other embodiments may provide a computer readable device and/or a non-transitory computer readable medium, and/or a machine readable device and/or a non-transitory machine readable medium, having stored thereon, a machine code and/or a computer program having at least one code section executable by a machine and/or a computer, thereby causing the machine and/or computer to perform the steps as described herein for presenting rotation previews of an object depicted in a volume rendering of 3D and/or 4D image data.

Accordingly, the present disclosure may be realized in hardware, software, or a combination of hardware and software. The present disclosure may be realized in a centralized fashion in at least one computer system, or in a distributed fashion where different elements are spread across several interconnected computer systems. Any kind of computer system or other apparatus adapted for carrying out the methods described herein is suited.

Various embodiments may also be embedded in a computer program product, which comprises all the features enabling the implementation of the methods described herein, and which when loaded in a computer system is able to carry out these methods. Computer program in the present context means any expression, in any language, code or notation, of a set of instructions intended to cause a system having an information processing capability to perform a particular function either directly or after either or both of the following: a) conversion to another language, code or notation; b) reproduction in a different material form.

While the present disclosure has been described with reference to certain embodiments, it will be understood by those skilled in the art that various changes may be made and equivalents may be substituted without departing from the scope of the present disclosure. In addition, many modifications may be made to adapt a particular situation or material to the teachings of the present disclosure without departing from its scope. Therefore, it is intended that the present disclosure not be limited to the particular embodiment disclosed, but that the present disclosure will include all embodiments falling within the scope of the appended claims.

What is claimed is:

1. A method comprising:
  presenting, by at least one processor, a volume rendering of an object having an initial viewing direction at a display system;
  presenting, by the at least one processor, a plurality of volume rendering previews of the object at the display system, wherein each of the plurality of volume rendering previews provides a different rotational viewing direction of the object different from the initial viewing direction of the object, and wherein each of the plurality of volume rendering previews is located on the display system in relation to the volume rendering at a position associated with a different one of a plurality of directional directives of a user input device;

receiving, by the at least one processor, a directional directive from the user input device, wherein the directional directive corresponds with one of the plurality of directional directives, and wherein the directional directive is an instruction to rotate the initial viewing direction of the volume rendering of the object in one of a plurality of rotational directions towards one of the plurality of volume rendering previews to achieve an updated viewing direction of the object rotated in a direction corresponding to the directional directive; and presenting, by the at least one processor, an updated volume rendering of the object at the display system, the updated volume rendering having the updated viewing direction of the object rotated from the initial viewing direction based on the directional directive from the user input device.

2. The method of claim 1, wherein the volume rendering is an ultrasound image.

3. The method of claim 1, comprising rendering, by the at least one processor, a three-dimensional (3D) or four-dimensional (4D) volume to generate the volume rendering and the updated volume rendering.

4. The method of claim 1, wherein the different rotational viewing direction of the object is provided for each of the plurality of volume rendering previews by offsetting a viewing angle from the initial viewing direction by a pre-defined amount.

5. The method of claim 1, wherein the plurality of volume rendering previews are presented automatically.

6. The method of claim 1, wherein the plurality of volume rendering previews are presented in response to a user directive received from the user input device.

7. The method of claim 1, wherein the plurality of volume rendering previews are updated in lock step with the presentation of the updated volume rendering.

8. The method of claim 1, wherein the plurality of volume rendering previews are removed from the display system in response to the directional directive received from the user input device.

9. A system comprising:
a user input device configured to provide a directional directive;
at least one processor configured to:
present a volume rendering of an object having an initial viewing direction at a display system;
present a plurality of volume rendering previews of the object at the display system, wherein each of the plurality of volume rendering previews provides a different rotational viewing direction of the object different from the initial viewing direction of the object, and wherein each of the plurality of volume rendering previews is located on the display system in relation to the volume rendering at a position associated with a different one of a plurality of directional directives of the user input device;
receive the directional directive from the user input device, wherein the directional directive corresponds with one of the plurality of directional directives, and wherein the directional directive is an instruction to rotate the initial viewing direction of the volume rendering of the object in one of a plurality of rotational directions towards one of the plurality of volume rendering previews to achieve an updated viewing direction of the object rotated in a direction corresponding to the directional directive; and
present an updated volume rendering of the object at the display system, the updated volume rendering having the updated viewing direction of the object rotated from the initial viewing direction based on the directional directive from the user input device; and
the display system configured to display the volume rendering, the plurality of volume rendering previews, and the updated volume rendering.

10. The system of claim 9, wherein the system is an ultrasound system or a medical workstation.

11. The system of claim 9, wherein the at least one processor is configured to provide the different rotational viewing direction of the object for each of the plurality of volume rendering previews by offsetting a viewing angle from the initial viewing direction by a pre-defined amount.

12. The system of claim 9, wherein the at least one processor is configured to automatically present the plurality of volume rendering previews.

13. The system of claim 9, wherein the user input device is configured to provide a user directive, and wherein the at least one processor is configured to present the plurality of volume rendering previews in response to the user directive received from the user input device.

14. The system of claim 9, wherein the at least one processor is configured to update the plurality of volume rendering previews in lock step with the presentation of the updated volume rendering.

15. The system of claim 9, wherein the at least one processor is configured to cease displaying the plurality of volume rendering previews at the display system in response to the directional directive received from the user input device.

16. A non-transitory computer readable medium having stored thereon, a computer program having at least one code section, the at least one code section being executable by a machine for causing the machine to perform steps comprising:
presenting a volume rendering of an object having an initial viewing direction at a display system;
presenting a plurality of volume rendering previews of the object at the display system, wherein each of the plurality of volume rendering previews provides a different rotational viewing direction of the object different from the initial viewing direction of the object, and wherein each of the plurality of volume rendering previews is located on the display system in relation to the volume rendering at a position associated with a different one of a plurality of directional directives of a user input device;
receiving a directional directive from the user input device, wherein the directional directive corresponds with one of the plurality of directional directives, and wherein the directional directive is an instruction to rotate the initial viewing direction of the volume rendering of the object in one of a plurality of rotational directions towards one of the plurality of volume rendering previews to achieve an updated viewing direction of the object rotated in a direction corresponding to the directional directive; and
presenting an updated volume rendering of the object at the display system, the updated volume rendering having the updated viewing direction of the object rotated from the initial viewing direction based on the directional directive from the user input device.

17. The non-transitory computer readable medium of claim 16, comprising offsetting a viewing angle from the initial viewing direction by a pre-defined amount to provide the different rotational viewing direction of the object for each of the plurality of volume rendering previews.

18. The non-transitory computer readable medium of claim 16, wherein the plurality of volume rendering previews are presented in response to a user directive received from the user input device.

19. The non-transitory computer readable medium of claim 16, comprising updating the plurality of volume rendering previews in lock step with the presentation of the updated volume rendering.

20. The non-transitory computer readable medium of claim 16, comprising removing the plurality of volume rendering previews from the display system in response to the directional directive received from the user input device.

\* \* \* \* \*